US009151764B2

(12) United States Patent
Crane et al.

(10) Patent No.: US 9,151,764 B2
(45) Date of Patent: Oct. 6, 2015

(54) BARRIER LAYER FOR GLUCOSE SENSOR

(75) Inventors: Barry Colin Crane, Shennington (GB);
William Paterson, Didcot (GB); Bruce Culbert, Bucks (GB)

(73) Assignee: Lightship Medical Limited, London (GB)

(*) Notice: Subject to any disclaimer, the term of this patent is extended or adjusted under 35 U.S.C. 154(b) by 0 days.

(21) Appl. No.: 13/578,893

(22) PCT Filed: Feb. 15, 2011

(86) PCT No.: PCT/GB2011/000209
§ 371 (c)(1),
(2), (4) Date: Nov. 2, 2012

(87) PCT Pub. No.: WO2011/101626
PCT Pub. Date: Aug. 25, 2011

(65) Prior Publication Data
US 2013/0040404 A1 Feb. 14, 2013

Related U.S. Application Data

(60) Provisional application No. 61/304,971, filed on Feb. 16, 2010.

(51) Int. Cl.
*G01N 33/66* (2006.01)
*B01D 63/00* (2006.01)
*A61B 5/145* (2006.01)
*A61B 5/1459* (2006.01)
*G01N 21/77* (2006.01)

(52) U.S. Cl.
CPC .............. *G01N 33/66* (2013.01); *A61B 5/1459* (2013.01); *A61B 5/14532* (2013.01); *B01D 63/00* (2013.01); *G01N 21/7703* (2013.01); *B01L 2200/027* (2013.01); *G01N 2021/772* (2013.01); *G01N 2021/775* (2013.01); *G01N 2021/7786* (2013.01); *Y10T 29/49826* (2015.01)

(58) Field of Classification Search
None
See application file for complete search history.

(56) References Cited

U.S. PATENT DOCUMENTS

| 3,975,350 | A |  | 8/1976 | Hudgin et al. |
|---|---|---|---|---|
| 4,618,533 | A | * | 10/1986 | Steuck .................... 428/315.7 |
| 4,938,870 | A | * | 7/1990 | Butler et al. ................. 210/490 |
| 5,468,390 | A |  | 11/1995 | Crivello et al. |
| 5,629,084 | A | * | 5/1997 | Moya ........................ 428/315.7 |
| 5,741,852 | A | * | 4/1998 | Marchant et al. ............ 525/54.3 |
| 6,002,954 | A | * | 12/1999 | Van Antwerp et al. ....... 600/317 |
| 6,193,077 | B1 |  | 2/2001 | Witham et al. |
| 6,387,672 | B1 |  | 5/2002 | Arimori et al. |
| 2002/0043651 | A1 |  | 4/2002 | Darrow et al. |
| 2006/0083688 | A1 | * | 4/2006 | Singaram et al. ............. 424/9.6 |
| 2008/0176271 | A1 | * | 7/2008 | Silver et al. .................... 435/29 |
| 2008/0214912 | A1 |  | 9/2008 | Cano |
| 2010/0055188 | A1 | * | 3/2010 | Ahn ............................ 424/489 |

FOREIGN PATENT DOCUMENTS

| JP | 2003-517588 | 5/2003 |
|---|---|---|
| JP | 2004-526497 | 9/2004 |
| JP | 2004-536279 | 12/2004 |
| JP | 2005-315871 A | 11/2005 |
| JP | 2008-209204 A | 9/2008 |
| JP | 2009-543031 T | 12/2009 |
| WO | WO 2006122554 A2 * | 11/2006 |
| WO | WO 2008/141241 | 11/2008 |
| WO | WO 2009/009756 | 1/2009 |
| WO | WO 2009/019470 | 2/2009 |
| WO | WO 2009/067626 | 5/2009 |
| WO | WO 2010/116142 | 10/2010 |
| WO | WO 2011/101624 | 8/2011 |

OTHER PUBLICATIONS

International Search Report and Written Opinion in International Application No. PCT/GB2011/000209, dated Jun. 1, 2011, 9 pages.
Adhikari and Majumdar, "Polymers in sensor applications," *Progress in Polymer Science*, 2004, 29(1):699-766.
Hester et al., "ATRP of Amphiphilic Graft Copolymers Based on PVDF and their use as Membrane Additives," *Macromolecules*, 2002, 35:7652-61.
Higuchi et al., "Separation of proteins by surface modified polysulfone membranes," *J Member Sci.*, 1991, 57:175-185.
Park et al., "Polysulfone-graft-poly(ethylene glycol) graft copolymers for surface modification of polysulfone membranes," *Biomaterials*, 2006, 27:856-865.
Ulbricht et al., "Surface modification of ultrafiltration membranes by low temperature plasma II. Graft polymerization onto polyacrylonitrile and polysulfone," *J Member Sci.*, 1996, 111:193-215.
Ulbricht, "Advanced functional polymer membranes," *Polymer*, 2006, 47(7):2217-2262.
Wang et al., "Synthesis and Performance of Novel Hydrogels Coatings for Implantable Glucose Sensors," *Biomacromolecules*, 2008, 9:561-567.
Yu et al., "Use of hydrogel to improve the performance of implanted glucose sensors," *Biosensors & Bioelectronics*, 2008, 23:1278-1284.

* cited by examiner

*Primary Examiner* — Galina Yakovleva
*Assistant Examiner* — Andrea S Grossman
(74) *Attorney, Agent, or Firm* — Fish & Richardson P.C.

(57) ABSTRACT

An optical glucose sensor comprising: a sensing region comprising a boronic acid receptor for binding to glucose and a fluorophore associated with said receptor; an optical waveguide for directing incident light onto the sensing region; and a hydrophilic, polymeric, glucose-permeable barrier layer which is provided on at least a part of the sensing region; wherein the sensor is adapted so that glucose enters the sensing region of the sensor through said barrier layer.

15 Claims, 3 Drawing Sheets

BARRIER LAYER FOR GLUCOSE SENSOR

This application is the U.S. national stage under 35 USC §371 of International Application Number PCT/GB2011/000209, filed on 15 Feb. 2011, which claims priority to U.S. Application No. 61/304,971, filed on 16 Feb. 2010, the entire contents of which is hereby incorporated by reference.

FIELD OF THE INVENTION

The invention relates to glucose sensors, methods for making such glucose sensors and methods for detecting or determining the quantity of glucose in a sample.

BACKGROUND TO THE INVENTION

It has been known for some time that boronates form reversible 5 membered ring complexes with saccharides. More recently, this property of boronates has been utilised in the development of sensors for the measurement of glucose in biological fluids. For example, a sensor may comprise a glucose receptor (the boronic acid) and a fluorophore that acts as the transmitter of the signal. These indicator chemistries can readily be immobilised onto an optical fibre of appropriate diameter, which can then be placed into body fluids or tissue to measure glucose.

It has been known for some time that boronic acids reversibly complex with glycoylated and glycated proteins. Although attempts have been made to devise sensing boronic acid chemistries that are selective it is obvious that glycated proteins represent potential interferents in the determination of glucose in body fluids when boronic acids are used as the sensor. Also other middle to high molecular weight endogenous materials have the potential to interfere with the boronic acid receptor by acting as quenchers of the transmitting fluorophore. There is therefore a need for a means to eliminate these interferents from a glucose sensor using boronic acid/fluorophore indicating chemistry.

SUMMARY OF THE INVENTION

The invention addresses the above-described problem by sheathing the boronic acid/fluorophore glucose indicating chemistry with a protective barrier layer which is permeable to glucose but which restricts the passage of large molecular weight molecules such as proteins and glycated proteins. Accordingly, the present invention provides an optical glucose sensor comprising
  a sensing region comprising a boronic acid receptor for binding to glucose and a fluorophore associated with said receptor;
  an optical waveguide for directing incident light onto the sensing region; and
  a hydrophilic, polymeric, glucose-permeable barrier layer which is provided on at least a part of the sensing region;
wherein the sensor is adapted so that glucose enters the sensing region of the sensor through said barrier layer.

The barrier layer is capable of restricting the passage of proteins and glycated proteins into the sensing region. Typically, the barrier layer is substantially impermeable to proteins and glycated proteins. For example, the barrier layer may restrict or prevent the passage of, or be substantially impermeable to, molecules having a molecular weight of greater than 6000, preferably greater than 5000, more preferably greater than 4000.

In a preferred embodiment, the barrier layer is provided by a semi-permeable membrane, for example a dialysis membrane. The pore size of the membrane can be selected so as to ensure permeability to glucose but to restrict or prevent the passage of larger macromolecules such as proteins and glycated proteins. Use of a dialysis membrane having a molecular weight cut off (MWCO) of from 1000 to 5000 eliminates potential interferents such as insulin, beta-microglobulin and albumin and their glycated derivatives.

In a particular aspect of this embodiment, a hydrophilic and/or negatively charged polymer is present within the pores of the membrane. This is typically achieved via in situ polymerisation, within the pores of the membrane, of a monomer mixture comprising one or more hydrophilic monomers and/or one or more negatively charged monomers. The resulting membrane is particularly effective as a barrier to proteins and glycated proteins due to its hydrophilicity and/or negative charge and has the further advantage that the polymerisation process may be used to control, and to further decrease, the pore size of the membrane.

In an alternative embodiment, the barrier layer is provided by a hydrogel. The highly hydrophilic nature of the hydrogel is particularly beneficial in repelling proteins and offering resistance to protein adsorption on the surface of the sensor.

The present invention also provides a method of detecting or quantifying the amount of glucose in a sample, comprising inserting into the sample a glucose sensor according to the invention, providing incident light to the sensing region of the sensor and detecting the emission pattern of the fluorophore.

Further preferred features and embodiments of the invention are described in the accompanying description and the appended claims.

DETAILED DESCRIPTION OF THE INVENTION

As used herein the term hydrophilic indicates a material which has an affinity for water. The glucose sensors of the invention are typically used to detect or quantify glucose in an aqueous solution. The hydrophilic barrier layer on the outside of the sensing region therefore has an affinity for the aqueous solution in which the glucose is dissolved. Further, the hydrophilicity of the barrier layer assists in repelling plasma proteins when a sensor is used in a bodily fluid, in particular in blood.

As used herein a glucose permeable barrier layer is a material which allows the passage of glucose through the layer but which restricts the passage of proteins and glycated proteins.

The present invention is envisaged for use with any optical glucose sensor using boronic acid/fluorophore glucose sensing chemistry. Fibre optic sensors are particularly envisaged, but the present invention may also be used with sensors having different types of optical waveguide. Glucose sensing is typically carried out in bodily fluids such as interstitial tissue or blood, although sensing of any aqueous solution may be carried out using the sensors of the invention. The particular embodiments described herein are envisaged for use as invasive sensors for insertion into a blood vessel. However, the present invention is not limited to such invasive sensors. Non-invasive sensors for in vitro use, implantable sensors and subcutaneous sensors are also within the scope of the present invention.

Figure 1:
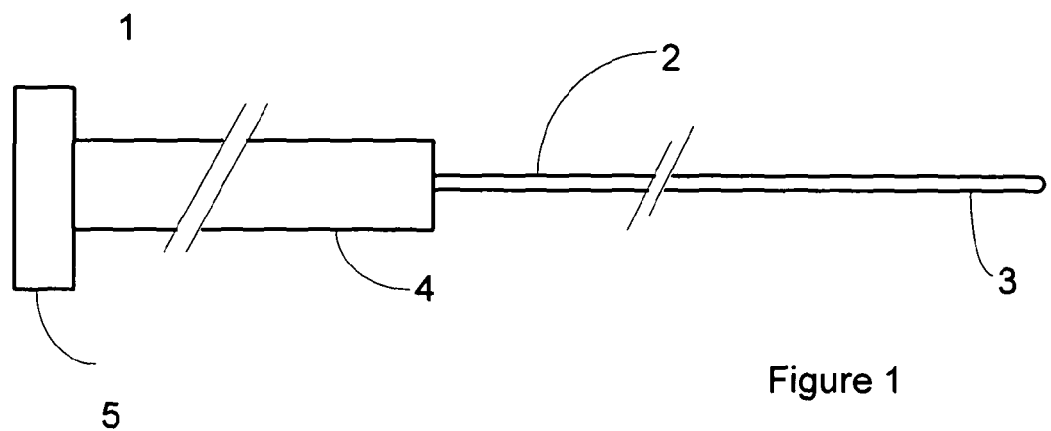
FIGS. 1 and 1a depict a sensor of the invention incorporating an optical fibre and a monitor for such a sensor.
Figure 1A:
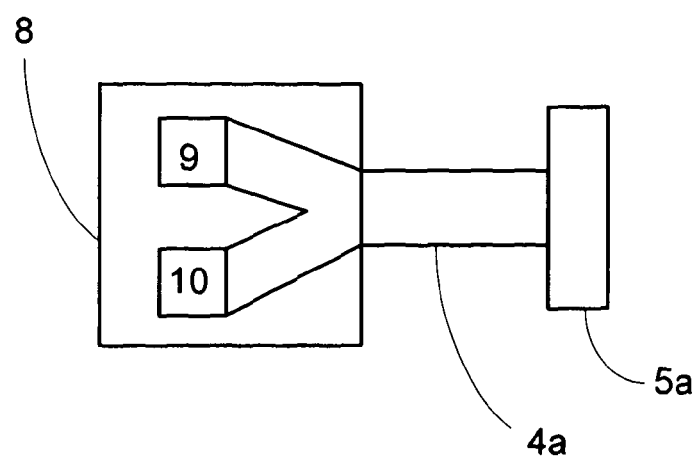

An example of a sensor of the invention incorporating an optical fibre is depicted in FIGS. 1 and 1a. The sensor 1 comprises an optical fibre 2 including a sensing region 3 at its distal end. In the case of an invasive sensor, fibre 2 is adapted for insertion into a patient, for example insertion into a blood vessel through a cannula. The sensing region 3 (depicted in more detail in FIGS. 2 and 3) contains a cell or chamber 7 in which the indicator chemistry is contained. The optical fibre extends through cable 4 to connector 5 which is adapted to mate with an appropriate monitor 8. The monitor typically includes further optical cable 4a that mates with the connector at 5a and at the other bifurcates to connect to (a) an appropriate source of incident light for the optical sensor 9 and (b) a detector for the return signal 10.

In one embodiment, the sensor of the invention is a disposable sensor. The sensor is typically adapted to be connected to a non-disposable monitor comprising a light source 9 and detector 10.

Figure 2:
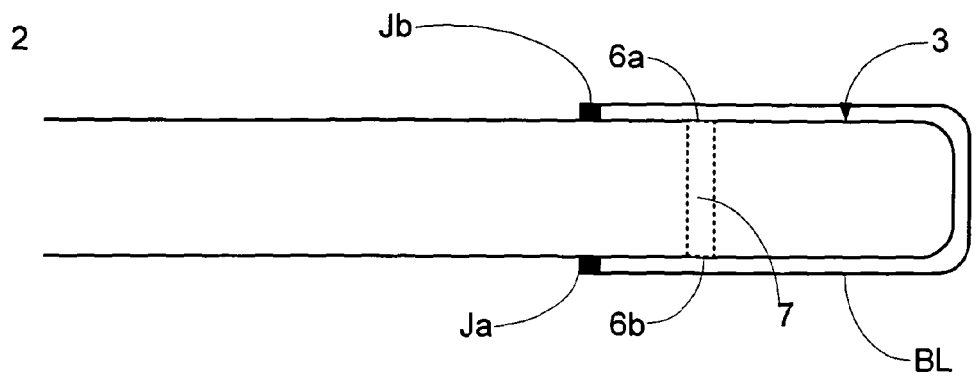
FIGS. 2 and 3 depict various embodiments of a sensing region of a sensor of the invention.

As depicted in FIG. 2, the sensing region 3 incorporates a cell 7 in the form of a chamber within the fibre. The cell may take any form, as long as it enables the indicator chemistry to be contained in the path of the incident light directed by the waveguide, here a fibre. Thus, the cell may be attached to the distal end of the fibre or waveguide or may be in the form of a chamber within the fibre having any desired shape.

The cell 7 contains the indicator chemistry, namely a boronic acid receptor for binding glucose and a fluorophore associated with the receptor. The emission pattern (e.g. the wavelength, intensity, lifetime) of the fluorophore is altered when the analyte is bound to the receptor allowing optical detection of glucose. The receptor and fluorophore may be directly bonded to one another as a receptor-fluorophore construct. Examples of suitable fluorophores include anthracene, pyrene and derivatives thereof. Examples of suitable boronic acid receptors are compounds having at least one, preferably two boronic acid groups.

In a preferred embodiment, the receptor is a group of formula (I)

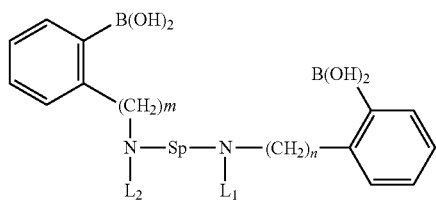

wherein m and n are the same or different and are typically one or two, preferably one; Sp is an aliphatic spacer, typically an alkylene moiety, for example a C1-C12 alkylene moiety, e.g. a C6 alkylene moiety; and L1 and L2 represent possible points of attachment to other moieties, for example to a fluorophore or to a hydrogel. For example, L1 and L2 may represent an alkylene, alkylene-arylene or alkylene-arylene-alkylene moiety, linked to a functional group. Where no attachment to another moiety is envisaged, the functional group is protected or replaced by a hydrogen atom. Typical alkylene groups for L1 and L2 are C1-C4 alkylene groups, e.g. methylene and ethylene. Typical arylene groups are phenylene groups. The functional group is typically any group which can react to form a bond with, for example, the fluorophore or hydrogel, e.g. ester, amide, aldehyde or azide.

Varying the length of the spacer Sp alters the selectivity of the receptor. Typically, a C6-alkylene chain provides a receptor which has good selectivity for glucose.

Further details of such receptors are found in U.S. Pat. No. 6,387,672, the contents of which are incorporated herein by reference in their entirety.

The receptor and fluorophore are typically bound to one another and may further be bound to a polymeric matrix. A hydrogel is an example of a suitable polymeric matrix.

Figure 3:
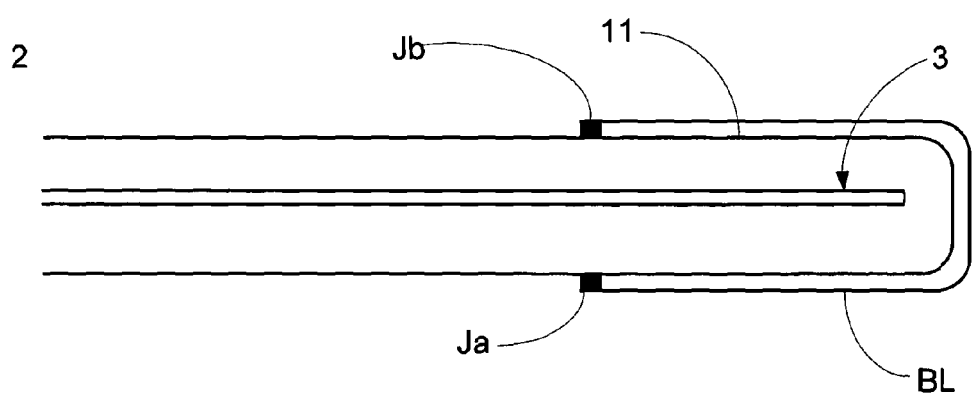

The sensing region 3 of the glucose sensor has one or more openings 6a, 6b to enable glucose to enter the cell. The barrier layer of the invention is typically provided across these openings so that glucose enters the cell through the barrier layer. In FIGS. 2 and 3, the barrier layer is provided over the entire sensing region 3. Alternatively, however, the barrier layer may be provided on only part of the sensing region, for example only across openings 6a and 6b.

The sensor is typically designed such that any openings into the sensing region through which glucose can pass are covered with the barrier layer. This ensures that protein adsorption is restricted at least at the openings into the sensing region. In a preferred embodiment, however, the entire sensing region, or the entire surface of the sensor which is to come into contact with the sample under test, is coated or sheathed with the barrier layer. This helps to prevent protein adsorption on any surface of the sensor and improves the biocompatibility of the sensor in the case of invasive or implantable sensors.

As depicted in FIG. 2, the barrier layer BL may be applied directly onto the sensing region, here onto the tip of the optical fibre. In an alternative embodiment depicted in FIG. 3, the sensing region 3 is provided within a separate support 11 and the barrier layer is provided on the support 11. The use of a separate support structure provides additional strength to the barrier layer which may itself be fragile. Holes or pores are provided in the support to enable glucose to enter the sensing region 3. Suitable support structures are polymer tubes which are perforated with holes, for example by laser ablation. Microporous hollow fibres which are commonly used in medical oxygenators and which have pores of approximately 0.2 micron in diameter provide appropriate support structures for use with fibre optic sensors. Alternative support structures are woven sheaths of polymeric or metallic materials such as those described in WO2009/019470, the contents of which are incorporated herein by reference in their entirety.

If desired, the barrier layer may be adhered to the surface of the sensor e.g. to the optical fibre itself or to support 11. This can be achieved by application of a suitable adherent such as cyanoacrylate. Alternatively, where the sensor surface and the barrier layer material are appropriate, the joint between the barrier layer and the sensor can be thermoformed, e.g. at Jo, Jb of FIGS. 2 and 3.

The barrier layer is formed from a polymeric material which is hydrophilic, permeable to glucose and which offers some restriction to the passage of high molecular weight materials such as proteins. In one embodiment, the barrier layer is a hydrogel. A hydrogel as used herein is a hydrophilic polymeric matrix which swells when placed in water. When placed in water, water is dispersed throughout the matrix. Examples of suitable hydrogel materials include cross-linked polyacrylamide, polydimethyl acrylamide, poly hydroxyl ethylmethacrylate, polyvinyl pyrrolidone, poly ethylene glycol acrylates and poly ethylene glycol methacrylates. The hydrogel is typically coated directly onto the outer surface of the sensing region, in the case of an optical fibre it is typically coated directly onto the tip of the optical fibre. The hydrogel barrier layer may incorporate additional materials such as anions, as described further below.

In an alternative embodiment, the barrier layer is formed by a semi-permeable membrane such as a dialysis membrane. Dialysis membranes are semi-permeable membranes that separate molecules by virtue of their size, shape, hydration and polarity. They are particularly suitable for use in the present invention since their pore size allows glucose to permeate the membrane but is too small to allow the passage of proteins. Dialysis membranes are usually in the form of hollow fibres and are available in materials such as polyarylethersulphone, polyimide, polycarbonate, polyacrylonitrile, polysulphone, polyethersulphone, polyvinylidenefluoride and cellulosic materials or mixtures or modifications thereof.

In another aspect of this embodiment, which is described in detail below, the semi-permeable membrane is formed from a microporous membrane having polymers incorporated within the pores of the membrane (e.g. by in situ polymerisation within the pores). The presence of the polymers within the pores causes a reduction in the pore size such that the membrane acts as a semi-permeable membrane, forming a barrier to high molecular weight materials such as proteins and glycated proteins. Microporous membranes suitable for use in this aspect typically have a pore size in the region of 0.1 to 10 µm, e.g. up to 2 µm or up to 1 µm, for example about 0.2 µm.

Semi-permeable membranes are available with different pore sizes relating to the molecular weight cut-off (MWCO) of the membrane. The molecular weight cut-off indicates the maximum molecular weight of molecule which can pass through the pores of the membrane. Small pore sizes are termed "low flux" with a low MWCO and a larger pore size is termed "high flux" with a high MWCO. Proteins are macromolecules that range in molecular weight from around 6,000 for insulin to 11,800 for beta-microglobulin, 66,200 for albumin to 970,000 for IGN. Thus to eliminate these potential interferents and their derivatives a low MWCO material should be chosen that does not allow materials of molecular weight 6,000 or higher to pass through but does allow glucose (MW 180) to pass. The pore size should, however, be maximised whilst eliminating these interferents in order to provide a maximum flux of glucose into the sensor.

In order to provide an acceptable response time for an intravascular sensor which continuously measures glucose, the membrane should preferably be selected so as to provide a 90% response time of no more than three minutes, preferably no more than two-and-a-half minutes. Preferred membranes have a MWCO of at least 1,000 and preferably no more than 5,000. For example, the MWCO may be at least 1,500 or at least 2,000, for example no more than 4,000. Preferred effective pore sizes (preferred pore sizes) are 1 to 20 nm, preferably 1 to 10 nm, for example about 6 nm.

In the embodiment of the invention described below in which polymerisation is carried out within the pores of the membrane, the polymerisation step decreases the effective MWCO and pore size of the membrane. The preferred MWCO and pore sizes described above refer to the final membrane for use in the glucose sensor and are therefore the effective MWCO and effective pore sizes of the resulting membrane following in situ polymerisation.

The sensor may be directly coated or sheathed with the membrane, but it is preferred that the membrane is provided on a support, e.g. a tube into which the sensor is placed (see FIG. 3). In one embodiment, the sensing region of the sensor is coated with a hydrogel and the membrane, e.g. the dialysis membrane barrier layer is placed onto the hydrogel layer.

Some of the materials used as dialysis membrane materials are inherently hydrophobic, for example polysulphone, polyethersulphone and polyvinylidenefluoride. In accordance with the present invention, the barrier layer is hydrophilic in order to avoid adsorption of serum proteins onto the layer. Materials which are by nature hydrophobic are therefore modified in order to provide some hydrophilic character, for example by grafting hydrophilic groups to the polymer or graft polymerisation using hydrophilic monomers. Suitable hydrophilic groups and monomers include 2-hydroxy-ethyl methacrylate, (meth)acrylic acid and hydroxyl- or sulphonyl-bearing groups or monomers.

Graft polymerisation can be achieved in accordance with the techniques of M Belfort et al. (J Membr Sci. 1996. 111. 193-215). This describes the use of radiation techniques to graft polymerise hydrophilic monomers such as 2-hydroxyethyl methacrylate, acylic acid, and methacrylic acid onto polysulphone membrane surfaces, which resulted in membranes with an increased flux. Alternative techniques are described by Higuchiet et al. (J. Membr Sci. 1991. 57. 175-185.) in which sulphonyl and hydroxyl end-terminated groups are chemically grafted to polysulphone membrane surfaces leading to reduced protein adsorption.

Hydrophilic membranes may alternatively be provided by the use of amphiphilic graft or comb polymers as surface modifying additives for the membranes (Mayes et al. Macromolecules. 2002. 35. 7652-61.). Similarly, polyethylene glycol groups can be incorporated into a polysulphone polymer as described by Mayes et al. (Biomaterials. 2006. 27. 856-865.). These membranes have shown significant resistance to protein adsorption and cell attachment. Examples of suitable membranes are those described in U.S. Pat. No. 6,193,077. These are non-cracking hydrophilic macroporous (0.1 to 100 micron pores) polyether sulphone membranes prepared by coating the surface with an aqueous solution of a preformed high molecular weight polyalkylene oxide polymer (25,000 to 1,000,000 daltons) and a polyfunctional monomer followed by plasma polymerisation. Further examples of suitable membranes are those described in U.S. Pat. No. 5,468,390. These membranes are arylpolysulphone membranes which have been modified by polymerising monofunctional monomers onto the surface without the use of an initiator.

In an alternative embodiment, hydrophilic character is provided by incorporating one or more hydrophilic polymers during wet spinning formation of a dialysis membrane. Dialysis membranes are typically produced by spinning a solution of an appropriate polymer in order to form the desired membrane structure (e.g. a hollow fibre dialysis membrane, which can be used to sheath the sensor). In this embodiment, a hydrophilic polymer is added to the polymer solution prior to spinning, thus leading to a dialysis membrane formed of the main membrane polymer(s) (e.g. polysulphone, polyethersulphone or polyvinylidene fluoride) as well as the hydrophilic polymer(s). The resulting membrane accordingly comprises hydrophilic areas or pockets which allow water to pass through. The hydrophilicity of the resulting membrane can be controlled by varying the amount of hydrophilic polymer which is incorporated. Typically, hydrophilic polymer makes up about 10% of the total polymer content of the solution prior to spinning.

A hydrophilic polymer as used herein is a polymer comprising units having hydrophilic character, for example, which is prepared from a mixture of monomers wherein at least one of the monomers has hydrophilic character.

Examples of suitable hydrophilic polymers are polyethylene glycol, polyethylene oxide and polyvinylpyrrolidone.

In a further alternative embodiment, hydrophilic character is provided by provision of a hydrophilic polymer, typically having functional groups with known protein repelling characteristics, within the pores of the membrane. The provision of the polymer within the pores of the membrane is typically achieved by diffusing one or more suitable hydrophilic monomers into the membrane (e.g. pore size 6 to 20 nm) and initiating polymerisation, for example by applying UV activation in the presence of an initiator. This leads to polymerisation occurring within the pores of the membrane and the resulting polymer is trapped within the pores. If desired, the diffusion and polymerisation steps can be repeated one or more times to increase the amount of polymer formed within the membrane pores. The membrane is, for example, in the form of a hollow fibre dialysis membrane such that the resultant tube could be used to sheath the sensor providing the necessary barrier properties.

In an alternative aspect of this embodiment, the hydrophilic polymer is provided within the pores of a microporous membrane, e.g. a microporous hollow fibre (typical pore size 0.1 to 10 μm, e.g. up to 2 μm or up to 1 μm, for example about 0.2 μm). The inherent decrease in pore size caused by the in situ polymerisation within the membrane pores provides a membrane which is an appropriate barrier to interferents such as proteins and glycated proteins.

Where a microporous membrane is used, this may be applied onto a separate support 11 as depicted in FIG. 3. Alternatively the microporous membrane itself may function both as the support as well as the barrier layer.

In this embodiment, the functional group integrated into the membrane (e.g. microporous membrane or dialysis membrane) is preferably polyethylene glycol or polyethylene oxide which have known protein repelling characteristics. Suitable hydrophilic monomers for use in this embodiment therefore include polyethyleneglycol dimethacrylate, polyethyleneglycol dimethacrylamide, polyethylenglycol diacrylate and polyethyleneglycol diacrylamide, or a combination thereof. Polyethyleneglycol dimethacrylate is preferred. Polyethylene glycol dimethacrylate and polyethyleneglycol diacrylate, and various derivatives, of varying molecular weights can be readily obtained from Sigma-Aldrich, UK.

Typically, the polymerisation mixture which is diffused into the membrane pores comprises a chain extending monomer in addition to the hydrophilic monomer(s). Examples of suitable chain extenders include di(meth)acrylate and di(meth)acrylamide.

Membranes in accordance with this embodiment of the invention have been shown to provide significant inhibition to protein adsorption and enhancement as a barrier to boronic acid receptor/fluorophore interferents. In addition, such treated membranes provide the ability to decrease and to fine tune the membrane pore size. Since the hydrophilic monomer(s) are diffused into the pores of the membrane and polymerised in-situ, the pore size will decrease and hence the MWCO will decrease. This decrease in pore size provides a membrane which acts as a more efficient barrier to proteins and glycated proteins. Hence, by variation of the concentration of the diffusing monomer solution and crosslinker, and the number of times the diffusion and polymerisation is carried out, the pore size and MWCO can be adjusted and determined by experiment. MWCO can be determined by the diffusion of monodisperse materials of known molecular weights with a fluorescent molecule attached. Materials of gradually increasing molecular weight are passed through the membrane and the diffusion breakthrough can be determined using a fluorimeter as a detector. Examples of suitable monodisperse materials are fluorescein-labelled dextrans available from Sigma-Aldrich in a variety of molecular weights.

In a further aspect of the invention, the effectiveness of the barrier layer can be enhanced by incorporating a negative charge into the layer. Proteins are negatively charged at physiological pH so the incorporation of a negative charge into the barrier layer acts as a repellent to proteins including glycated proteins, or other negatively charged interferents. This can be achieved by incorporating a negatively charged monomer or polymer or an anion into the barrier layer.

Anions are particularly suitable for incorporation into a hydrogel barrier layer. Examples of suitable anions include halides, sulfonate, carboxylate, alkoxide.

Negatively charged monomers or polymers are suitable for incorporation into a membrane (e.g. microporous membrane or dialysis membrane) barrier layer. Suitable negatively charged monomers or polymers include potassium sulphopropylmethacrylate, acrylic or methacylic acids or their corresponding polymers.

In the case of a membrane barrier layer, negatively charged monomers or polymers can be grafted to the membrane itself. Alternatively, one or more negatively charged polymers can be incorporated into the polymer mixture during wet spinning formation of a dialysis membrane. This directly incorporates a negatively charged monomer into the membrane structure. One or more negatively charged polymers may be used alone, or in combination with one or more hydrophilic polymers.

Alternatively, one or more negatively charged monomer(s) such as potassium sulphopropylmethacrylate can be diffused into the membrane (e.g. microporous membrane or dialysis membrane) and then polymerised in situ. Polymerisation can be carried out in a similar manner to that discussed above with regard to hydrophilic monomers such as polyethyleneglycol dimethacrylate. This process leads to the formation of a negatively charged polymer which is trapped by virtue of its size, or through copolymerisation with hydrophilic monomers, within the pores of the membrane (e.g. microporous membrane or dialysis membrane). Such polymerisation may be carried out using one or more negatively charged monomers alone, or using a mixture of one or more hydrophilic monomers as described above and one or more negatively charged monomers.

In an alternative embodiment, the negatively charged material is heparin. This has the advantage that the negative charge carried on the heparin molecule repels proteins, but has the added benefit of being antithrombogenic. Heparin can be incorporated into a hydrogel or grafted to, or polymerised with, a membrane (e.g. microporous membrane or dialysis membrane).

The sensor is manufactured by providing a sensing region comprising a boronic acid receptor for binding to glucose and a fluorophore associated with said receptor; providing an optical waveguide for directing incident light onto the sensing region; and providing a hydrophilic, polymeric, glucose-permeable barrier layer on at least a part of the sensing region; and wherein the sensor is adapted so that glucose enters the sensing region of the sensor through said barrier layer.

In a particular embodiment, the barrier layer is a semipermeable membrane and the method comprises diffusing one or more monomers selected from hydrophilic and negatively charged monomers into the pores of the membrane (e.g. a dialysis membrane or a microporous membrane) and initiating polymerisation. This results in a hydrophilic and/or negatively charged polymer being formed within the pores of the membrane (e.g. the microporous or dialysis membrane) and a decrease in pore size. Polymerisation to form the hydrophilic or negatively charged polymer can be carried out either before or after applying the membrane (e.g. microporous membrane or dialysis membrane) to the sensing region of the sensor.

Example 1

A polyethersulphone hollow fibre dialysis membrane was dipped into a polymerisation mixture as set out below for 10 minutes and then polymerisation was initiated by UV at 240 nm for 30 seconds at a power setting of 8.3 milliwatts. The resultant membrane was washed in phosphate buffer solution at 37 C for 12 hours, rinsed in distilled water and then air dried.
Polymerisation Mixture
2.00 g Polyethylene glycoldimethacrylate(600)
1.00 g Dimethylacrylamide
0.50 g Potassium propylsulphomethacrylate
0.02 g Irgacure 651
0.20 g Triton X
3.50 Water The resultant membrane contains a polymer having units derived from dimethyl acrylamide, potassium sulphopropylmethacrylate, and crosslinked with polyethylene glycol dimethacrylate, within its pores.

The sensing region of a fibre optic glucose sensor utilising a diboronic acid/fluorophore indicator in accordance with those described in U.S. Pat. No. 6,387,672 was sheathed with the above membrane and used to determine glucose concentrations of human blood. For comparison, experiments in the same blood samples were also carried out using a sensor identical to that described above except that it is sheathed with unmodified polyethersulphone hollow fibre dialysis membrane.

The sensors were tested by excitation with an appropriate excitation wavelength and measurement of the emission signal from the sensor chemistry. A response curve to glucose was defined by varying the glucose concentration though three points, the curve was further defined by a set of three constants which allows the calculation of glucose concentration at any given measured emission intensity. The modulation is a measure of the intensity change for a given change in the glucose concentration and is hence a measure of the sensitivity of the sensor. An initial modulation was determined at zero time from a 3-point calibration in isotonic phosphate buffered saline and this was compared with modulations calculated from further 3-point calibrations following exposure of the sensors to human blood for both 5 and 20 hours. The results are depicted in FIG. 4.

Figure 4:
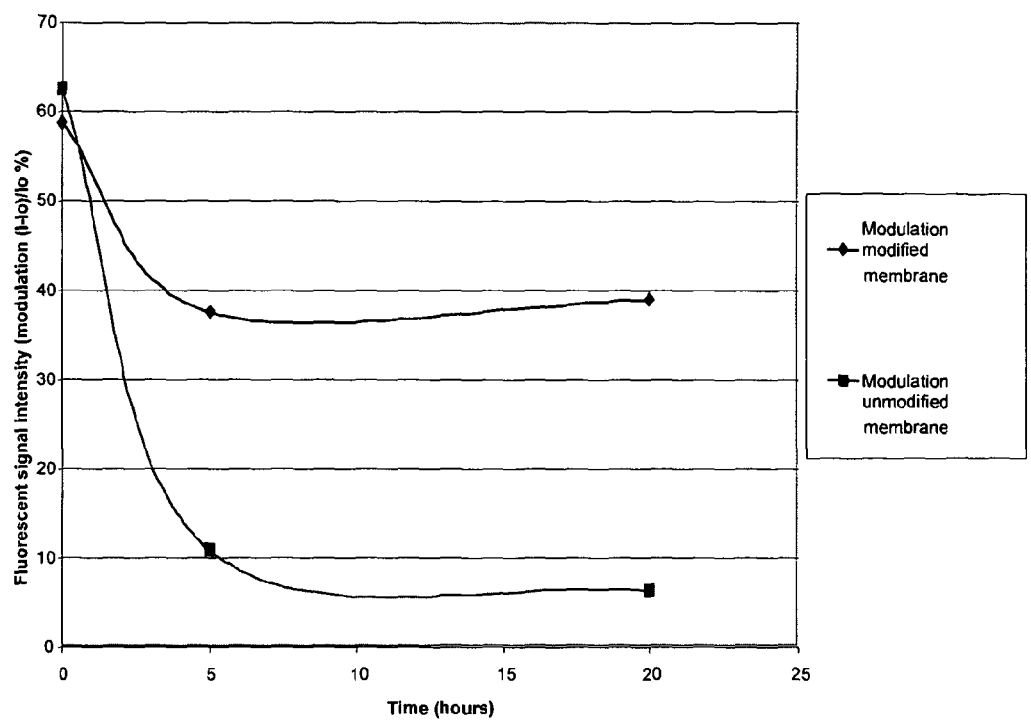
FIG. 4 shows a graph of the glucose calibration of a fibre optic sensor sheathed with a polyether sulphone hollow fibre dialysis membrane which is (a) modified by the in-situ polymerisation process described in Example 1 or (b) unmodified. The calibrations were run in human blood.

FIG. 4 shows comparatively the fluorescent signal intensity of each sensor. It can be seen that the decrease in fluorescent intensity with time is much greater for the sensor that has the unmodified membrane than that for the sensor with the modified membrane. The modified membrane has much better barrier properties to protein and glycated proteins that are present in human blood, resulting in significantly improved sensitivity of the sensor.

The present invention has been described with reference to a number of particular embodiments and examples. The invention is not, however, limited to these specific embodiments and examples.

The invention claimed is:

1. An optical glucose sensor comprising:
   a sensing region comprising a boronic acid receptor for binding to glucose and a fluorophore associated with said receptor;
   an optical waveguide for directing incident light onto the sensing region; and
   a hydrophilic, polymeric, glucose-permeable barrier layer which is provided on at least a part of the sensing region, the barrier layer comprising a semi-permeable membrane having a polymer which incorporates a negative charge within the pores of the membrane, the membrane being formed by generating the polymer in situ by diffusing a monomer incorporating a negative charge into the pores of a membrane and initiating polymerisation;
   wherein the sensor is adapted so that glucose enters the sensing region of the sensor through said barrier layer, and wherein the polymer which incorporates a negative charge does not comprise a boronic acid receptor or a fluorophore.

2. The glucose sensor according to claim 1, wherein the membrane restricts the passage of proteins and glycated proteins having a molecular weight of 5000 Da or greater.

3. The glucose sensor according to claim 1, wherein the membrane has an effective pore size of from 1 to 20 nm.

4. The glucose sensor according to claim 1 wherein a hydrophilic polymer is present within the pores of the membrane.

5. The glucose sensor according to claim 1, wherein the semi-permeable membrane is formed by diffusing a negatively charged monomer into the pores of a dialysis membrane and initiating polymerisation.

6. A glucose sensor according to claim 1, wherein the semi-permeable membrane is formed by diffusing a negatively charged monomer into the pores of a microporous membrane and initiating polymerisation.

7. The glucose sensor according to claim 1 wherein the barrier layer incorporates an anion or a negatively charged group or molecule.

8. The glucose sensor according to claim 1 wherein the barrier layer comprises heparin.

9. The glucose sensor according to claim 1 wherein the sensing region is provided within a support and the barrier layer is provided on said support.

10. A method of manufacturing a glucose sensor according to claim 1, which comprises
    providing a sensing region comprising a boronic acid receptor for binding to glucose and a fluorophore associated with said receptor;
    providing an optical waveguide for directing incident light onto the sensing region; and
    providing a hydrophilic, polymeric, glucose-permeable barrier layer on at least a part of the sensing region, the barrier layer comprising a semi-permeable membrane having a polymer which incorporates a negative charge within the pores of the membrane, the membrane being formed by generating the polymer in situ by diffusing a monomer incorporating a negative charge into the pores of a membrane and initiating polymerisation;
    wherein the sensor is adapted so that glucose enters the sensing region of the sensor through said barrier layer, and wherein the polymer which incorporates a negative charge does not comprise a boronic acid receptor or a fluorophore.

11. The method according to claim 10, wherein the method comprises diffusing negatively charged monomer(s) into the pores of a microporous membrane and initiating polymerisation.

12. The method according to claim 10, wherein the method comprises diffusing negatively charged monomer(s) into the pores of a dialysis membrane and initiating polymerisation.

13. The method according to claim 10, wherein the barrier layer is a dialysis membrane produced by spinning a polymer solution comprising at least one negatively charged polymer.

14. A method of detecting and/or quantifying the amount of glucose in a sample, comprising inserting into the sample a glucose sensor according to claim 1, providing incident light to the sensing region of the sensor and detecting the emission pattern of the fluorophore.

15. An optical glucose sensor comprising:
   a sensing region comprising a boronic acid receptor for binding to glucose and a fluorophore associated with said receptor;
   an optical waveguide for directing incident light onto the sensing region; and
   a hydrophilic, polymeric, glucose-permeable barrier layer which is provided on at least a part of the sensing region, the barrier layer comprising a semi-permeable membrane having a polymer which incorporates a negative charge within the pores of the membrane, the membrane being formed by generating the polymer in situ by diffusing a monomer incorporating a negative charge into the pores of a membrane and initiating polymerisation;
wherein the sensor is adapted so that glucose enters the sensing region of the sensor through said barrier layer, wherein the membrane restricts the passage of proteins and glycated proteins having a molecular weight of 6000 Da or greater, and wherein the polymer which incorporates a negative charge does not comprise a boronic acid receptor or a fluorophore.

* * * * *